United States Patent
Ouyang et al.

(10) Patent No.: US 10,292,571 B2
(45) Date of Patent: May 21, 2019

(54) HANDHELD SURGICAL ENDOSCOPE WITH WIDE FIELD OF VIEW (FOV) AND ILLUMINATION BRIGHTNESS ADJUSTED BY AREA WITHIN THE FOV

(71) Applicant: Uro Viu Corporation, Bellevue, WA (US)

(72) Inventors: Xiaolong Ouyang, Bellevue, WA (US); Robert K. Deckman, San Bruno, CA (US); Chih-Yu Ting, New Taipei (TW); Shih-Ping Wang, Palo Alto, CA (US)

(73) Assignee: UROVIU CORPORATION, Bellevue, WA (US)

( * ) Notice: Subject to any disclaimer, the term of this patent is extended or adjusted under 35 U.S.C. 154(b) by 0 days.

(21) Appl. No.: 15/855,532

(22) Filed: Dec. 27, 2017

(65) Prior Publication Data

US 2018/0132700 A1     May 17, 2018

Related U.S. Application Data

(63) Continuation-in-part of application No. 15/651,526, filed on Jul. 17, 2017, which is a continuation-in-part
(Continued)

(51) Int. Cl.
*A61B 1/05*     (2006.01)
*A61B 1/06*     (2006.01)
(Continued)

(52) U.S. Cl.
CPC ...... *A61B 1/00066* (2013.01); *A61B 1/00016* (2013.01); *A61B 1/00039* (2013.01);
(Continued)

(58) Field of Classification Search
CPC ............ A61B 1/00009; A61B 1/00052; A61B 1/00105; A61B 1/00108; A61B 1/00174;
(Continued)

(56) References Cited

U.S. PATENT DOCUMENTS

| 5,549,547 A | 8/1996 | Cohen et al. |
| 5,928,137 A | 7/1999 | Green |

(Continued)

FOREIGN PATENT DOCUMENTS

| WO | WO2012/060932 | 5/2012 |
| WO | WO2014/031192 | 2/2014 |

(Continued)

OTHER PUBLICATIONS

Jun. 6, 2018 International Search Report and Written Opinion in Connection with corresponding PCT International Application No. PCT/US2018/014880.
(Continued)

*Primary Examiner* — John P Leubecker
(74) *Attorney, Agent, or Firm* — Cooper & Dunham LLP

(57) ABSTRACT

A handheld surgical endoscope has a disposable, single-use portion that includes a and a re-usable portion that includes a handle and display module. The distal tip includes LED illumination and an imaging module that feeds live video to the display module. The imaging module includes a lens system of no more than two lenses and provides the imaging module with a field of view greater than 120 degrees, preferably 130 degrees or more, and most preferably 140 degrees or more. LED illumination is provided by plural LED arranged symmetrically around an optical axis to provide a field of illumination that substantially coincides with the field of view of an imaging module. An image brightness balance arrangement selectively varies the illumination provided by different LEDs to reduce brightness differences between different areas of the displayed images.

20 Claims, 14 Drawing Sheets

Related U.S. Application Data of application No. 15/462,331, filed on Mar. 17, 2017, which is a continuation-in-part of application No. PCT/US2016/065396, filed on Dec. 7, 2016, which is a continuation-in-part of application No. 15/371,858, filed on Dec. 7, 2016, now Pat. No. 9,895,048, said application No. 15/462,331 is a continuation-in-part of application No. 15/371,858, which is a continuation-in-part of application No. 14/913,867, filed on Feb. 23, 2016, said application No. 15/462,331 is a continuation-in-part of application No. 14/913,867, filed as application No. PCT/US2016/018670 on Feb. 19, 2016, said application No. PCT/US2016/065396 is a continuation-in-part of application No. PCT/US2016/018670, filed on Feb. 19, 2016, said application No. 15/462,331 is a continuation-in-part of application No. PCT/US2016/018670, filed on Feb. 19, 2016, said application No. 15/371,858 is a continuation-in-part of application No. PCT/US2016/018670, filed on Feb. 19, 2016.

(60) Provisional application No. 62/452,883, filed on Jan. 31, 2017, provisional application No. 62/449,257, filed on Jan. 23, 2017, provisional application No. 62/443,769, filed on Jan. 8, 2017, provisional application No. 62/416,403, filed on Nov. 2, 2016, provisional application No. 62/405,930, filed on Oct. 9, 2016, provisional application No. 62/375,814, filed on Aug. 16, 2016, provisional application No. 62/362,643, filed on Jul. 15, 2016, provisional application No. 62/339,810, filed on May 21, 2016, provisional application No. 62/299,453, filed on Feb. 24, 2016, provisional application No. 62/287,901, filed on Jan. 28, 2016, provisional application No. 62/279,784, filed on Jan. 17, 2016, provisional application No. 62/275,241, filed on Jan. 6, 2016, provisional application No. 62/275,222, filed on Jan. 5, 2016, provisional application No. 62/259,991, filed on Nov. 25, 2015, provisional application No. 62/254,718, filed on Nov. 13, 2015, provisional application No. 62/120,316, filed on Feb. 24, 2015, provisional application No. 62/119,521, filed on Feb. 23, 2015.

(51) Int. Cl.
*A61B 1/307* (2006.01)
*A61B 1/00* (2006.01)
*A61B 1/015* (2006.01)

(52) U.S. Cl.
CPC ...... *A61B 1/00048* (2013.01); *A61B 1/00052* (2013.01); *A61B 1/00103* (2013.01); *A61B 1/00105* (2013.01); *A61B 1/00108* (2013.01); *A61B 1/00119* (2013.01); *A61B 1/00135* (2013.01); *A61B 1/015* (2013.01); *A61B 1/051* (2013.01); *A61B 1/0623* (2013.01); *A61B 1/0676* (2013.01); *A61B 1/0684* (2013.01); *A61B 1/00034* (2013.01); *A61B 1/00128* (2013.01)

(58) Field of Classification Search
CPC ....... A61B 1/00163; A61B 1/05; A61B 1/051; A61B 1/0676; A61B 1/0684; A61B 1/307
See application file for complete search history.

(56) References Cited

U.S. PATENT DOCUMENTS

| | | |
|---|---|---|
| 5,935,141 A | 10/1999 | Weldon |
| 6,007,531 A | 12/1999 | Snoke |
| 6,017,322 A | 1/2000 | Snoke |
| 6,095,970 A * | 8/2000 | Hidaka ............ A61B 1/00124 600/109 |
| 6,210,416 B1 | 4/2001 | Chu et al. |
| 6,221,007 B1 | 4/2001 | Green |
| 6,261,226 B1 | 7/2001 | McKenna et al. |
| 7,798,995 B2 | 9/2010 | Yue |
| 7,946,981 B1 * | 5/2011 | Cubb ............... A61B 1/00052 600/120 |
| 8,052,609 B2 * | 11/2011 | Harhen ............ A61B 8/12 600/136 |
| 8,460,182 B2 | 6/2013 | Ouyang et al. |
| 8,803,960 B2 * | 8/2014 | Sonnenschein .... A61B 1/00096 348/76 |
| 2001/0007051 A1 * | 7/2001 | Nakashima ......... A61B 1/05 600/179 |
| 2003/0078476 A1 * | 4/2003 | Hill ................. A61B 1/00052 600/160 |
| 2003/0078502 A1 | 4/2003 | Miyaki et al. |
| 2005/0085695 A1 | 4/2005 | Sherner et al. |
| 2005/0154262 A1 * | 7/2005 | Banik .............. A61B 1/00059 600/179 |
| 2005/0177027 A1 * | 8/2005 | Hirata .............. A61B 1/0676 600/179 |
| 2006/0063976 A1 | 3/2006 | Aizenfeld et al. |
| 2006/0167340 A1 * | 7/2006 | Pease .............. A61B 1/00052 600/127 |
| 2006/0171693 A1 | 8/2006 | Todd et al. |
| 2006/0173245 A1 | 8/2006 | Todd et al. |
| 2007/0117437 A1 * | 5/2007 | Boehnlein ......... A61B 1/00052 439/210 |
| 2007/0162095 A1 * | 7/2007 | Kimmel ............ A61B 1/00089 600/109 |
| 2007/0167868 A1 | 7/2007 | Sauer |
| 2007/0197875 A1 | 8/2007 | Osaka |
| 2008/0071144 A1 * | 3/2008 | Fein ................ A61B 1/00167 600/178 |
| 2008/0108869 A1 * | 5/2008 | Sanders ........... A61B 1/00105 600/109 |
| 2008/0225410 A1 * | 9/2008 | Ning .............. A61B 1/00096 359/782 |
| 2008/0255416 A1 | 10/2008 | Gilboa |
| 2009/0076321 A1 | 3/2009 | Suyama |
| 2009/0080214 A1 | 3/2009 | Watanabe |
| 2009/0118580 A1 | 5/2009 | Sun |
| 2010/0191053 A1 * | 7/2010 | Garcia ............. A61B 1/00105 600/109 |
| 2011/0009694 A1 | 1/2011 | Schultz |
| 2011/0063428 A1 * | 3/2011 | Sonnenschein .... A61B 1/00096 348/76 |
| 2012/0040305 A1 * | 2/2012 | Karazivan ......... A61B 1/00087 433/29 |
| 2012/0289858 A1 * | 11/2012 | Ouyang ........... A61B 10/0275 600/562 |
| 2013/0035553 A1 * | 2/2013 | Konstorum ....... A61B 1/00066 600/156 |
| 2013/0172676 A1 | 7/2013 | Levy et al. |
| 2013/0225921 A1 | 8/2013 | Liu |
| 2013/0345514 A1 | 12/2013 | Manion |
| 2014/0022649 A1 * | 1/2014 | Eckhardt ............ G02B 17/08 359/728 |
| 2014/0107416 A1 * | 4/2014 | Birnkrant .......... A61B 1/00016 600/110 |
| 2014/0180007 A1 * | 6/2014 | Edidin ............... A61B 1/05 600/122 |
| 2014/0213848 A1 | 7/2014 | Moskowitz |
| 2014/0228635 A1 * | 8/2014 | Tuliakov ............ A61B 1/06 600/109 |
| 2014/0323991 A1 | 10/2014 | Tang et al. |

(56) References Cited

U.S. PATENT DOCUMENTS

| | | | |
|---|---|---|---|
| 2015/0005575 A1* | 1/2015 | Kobayashi | A61B 1/00009 600/103 |
| 2015/0018622 A1 | 1/2015 | Tesar et al. | |
| 2015/0164313 A1 | 6/2015 | Ouyang et al. | |
| 2016/0073853 A1* | 3/2016 | Venkatesan | A61B 1/0607 348/68 |
| 2016/0174819 A1 | 6/2016 | Ouyang et al. | |
| 2016/0367119 A1 | 12/2016 | Ouyang et al. | |
| 2017/0310858 A1* | 10/2017 | Mueckl | G02B 23/2476 |

FOREIGN PATENT DOCUMENTS

| | | |
|---|---|---|
| WO | WO2014/065901 | 5/2015 |
| WO | WO 2016/040131 A1 | 3/2016 |

OTHER PUBLICATIONS

Information Disclosure Statement submitted Aug. 17, 2016 in connection with U.S. Appl. No. 14/913,867.

Information Disclosure Statement submitted Mar. 23, 2017 in connection with U.S. Appl. No. 15/371,858, now U.S. Pat. No. 9,895,048 B2.

List of References dated Dec. 29, 2017 in connection with U.S. Appl. No. 15/371,858, now U.S. Pat. No. 9,895,048 B2.

List of References dated Jan. 24, 2018 in connection with U.S. Appl. No. 15/371,858, now U.S. Pat. No. 9,895,048 B2.

Information Disclosure Statement submitted Mar. 23, 2017 in Connection with U.S. Appl. No. 15/462,331.

Information Disclosure Statement submitted Dec. 13, 2017 in connection with U.S. Appl. No. 15/651,526.

Information Disclosure Statement submitted Jan. 16, 2018 in connection with U.S. Appl. No. 15/651,526.

Jul. 12, 2016 International Search Report and Written Opinion in Connection with corresponding PCT International Application No. PCT/US2016/018670.

Feb. 24, 2017 International Search Report and Written Opinion in Connection with corresponding PCT International Application No. PCT/US2016/065396.

Jul. 12, 2016 International Search Report and Written Opinion in connection with corresponding International Application No. PCT/US2016/18670.

* cited by examiner

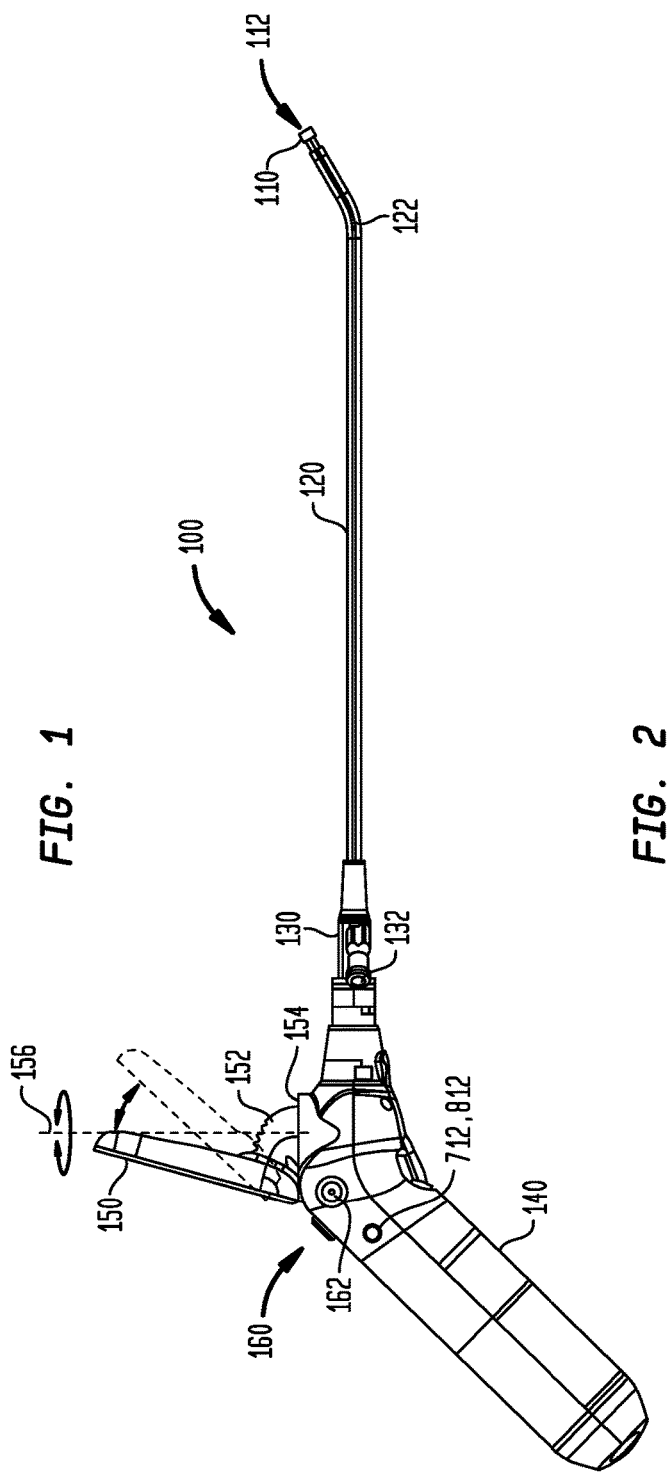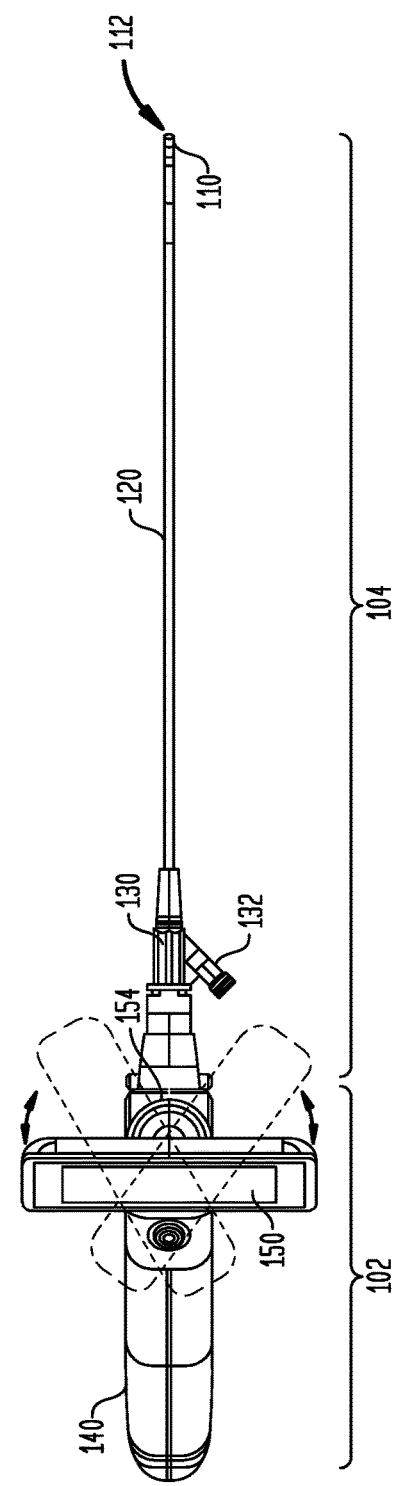

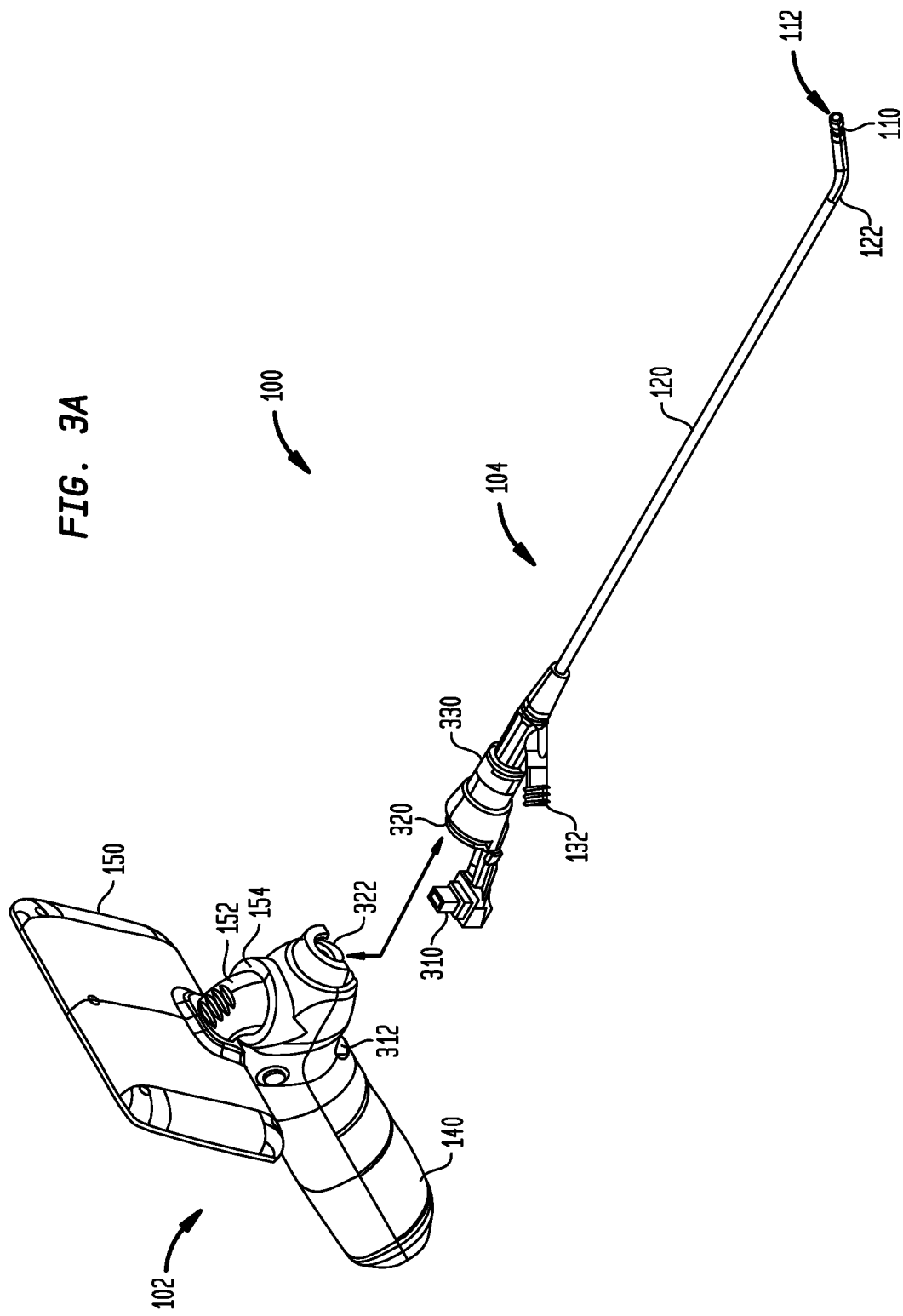

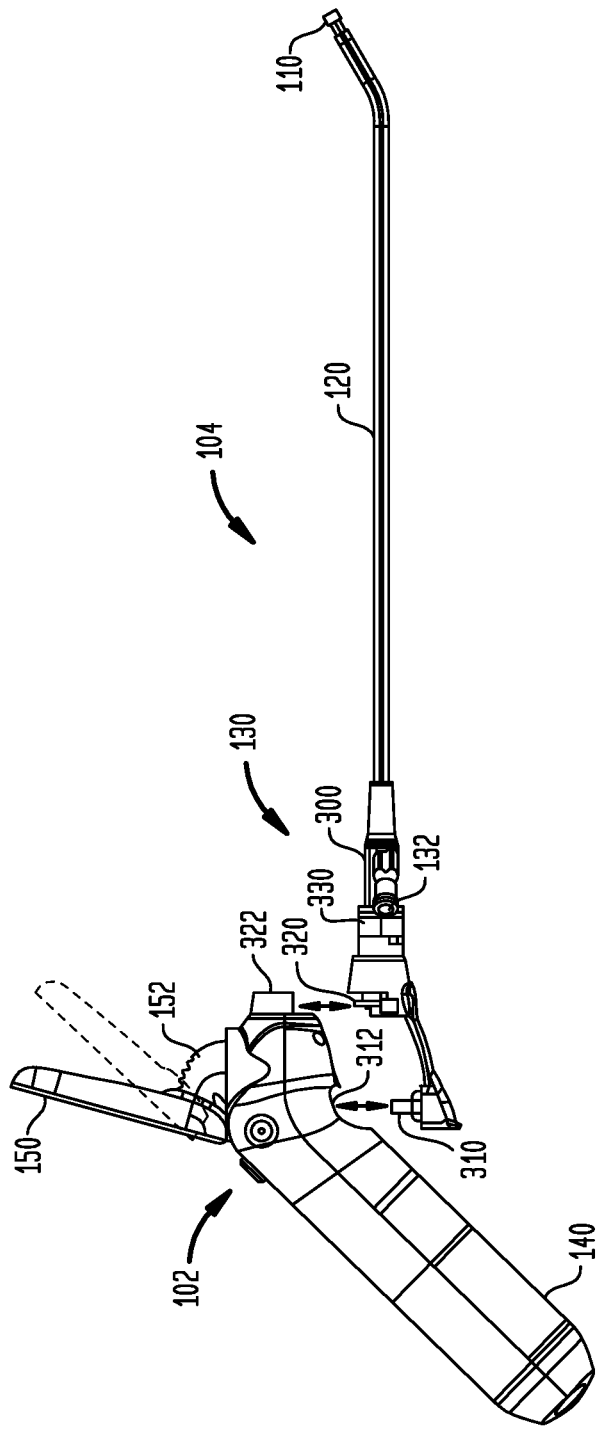

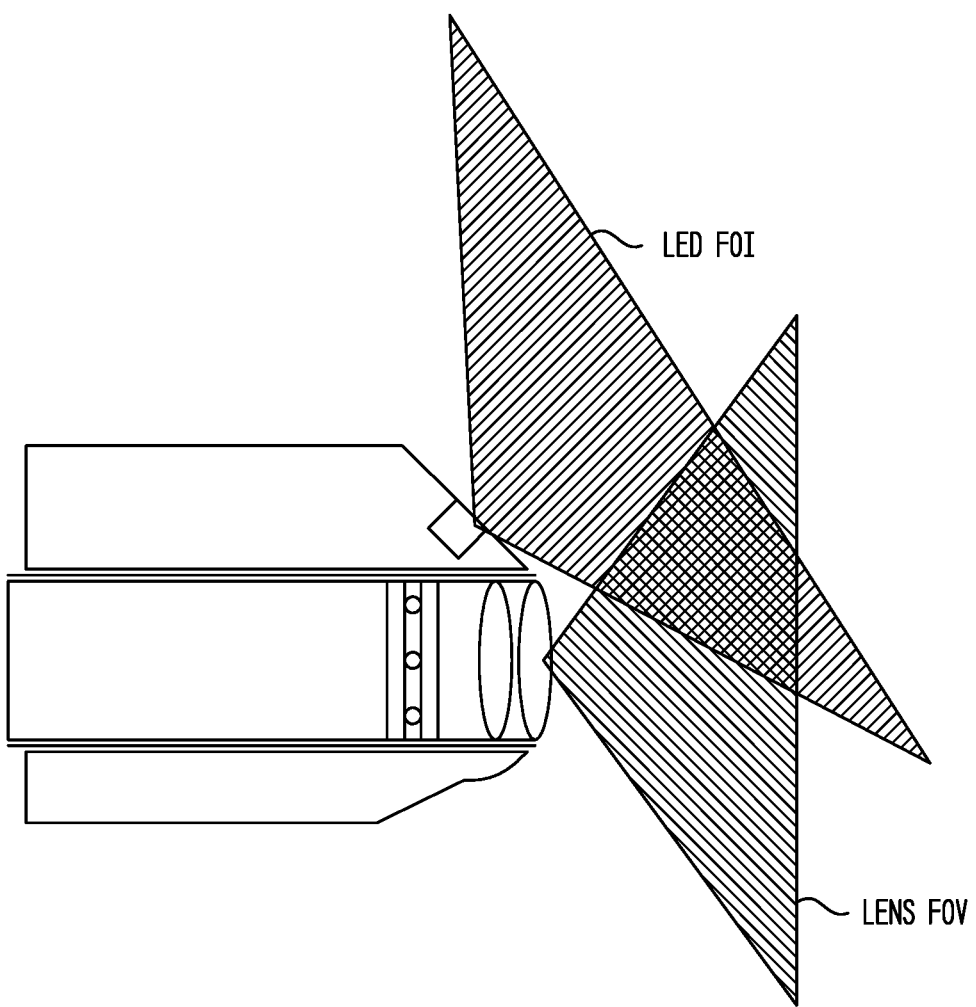

HANDHELD SURGICAL ENDOSCOPE WITH WIDE FIELD OF VIEW (FOV) AND ILLUMINATION BRIGHTNESS ADJUSTED BY AREA WITHIN THE FOV

REFERENCE TO RELATED APPLICATIONS

This patent application claims the benefit of and incorporates by reference each of the following provisional applications:
U.S. Prov. Ser. No. 62/573,380 filed Oct. 17, 2017; and
U.S. Prov. Ser. No. 62/578,407 filed Oct. 28, 2017;
U.S. Prov. Ser. No. 62/443,769 filed Jan. 8, 2017;
U.S. Prov. Ser. No. 62/449,257 filed Jan. 23, 2017; and
U.S. Prov. Ser. No. 62/452,883 filed Jan. 31, 2017.
U.S. Prov. Ser. No. 62/513,386 filed May 31, 2017;
U.S. Ser. No. 62/530,238 filed Jul. 9, 2017; and
U.S. Prov. Ser. No. 62/531,212 filed Jul. 11, 2017.

This patent application is a continuation-in-part of U.S. Ser. No. 15/651,526 filed Jul. 17, 2017, which is a continuation-in-part of U.S. Ser. No. 15/462,331 filed Mar. 17, 2017, which in turn is a continuation-in-part of each of (1) U.S. Ser. No. 15/371,858 filed Dec. 7, 2016, now U.S. Pat. No. 9,895,048, (2) U.S. Ser. No. 14/913,867 filed Feb. 23, 2016, (3) PCT/US16/65396 filed Dec. 7, 2016, and (4) PCT/UC16/18670 filed Feb. 19, 2016.

PCT/US16/65396 is a continuation-in-part of each of (1) U.S. Ser. No. 15/913,867, and (2) PCT/UC16/18670 is a National Stage of PCT/UC16/18670.

Each of the non-provisional U.S. application and PCT applications identified above claims the benefit of a respective plurality of provisional U.S. applications.

This application incorporates by reference each of the non-provisional U.S. applications and PCT applications identified above, and each of the provisional U.S. applications the benefits of which is claimed in each of said non-provisional U.S. applications and PCT applications identified above.

FIELD

This patent specification relates mainly to a medical device for use in tissue examinations and endoscopic surgery such as in urology. More particularly, some embodiments relate to an integrated, handheld, low-cost surgical endoscope device having a single-use portion and a multiple-use portion, and having a uniquely wide field of view (FOV) and/or illumination brightness adjusted as needed by area within the FOV.

BACKGROUND

Conventional endoscopes commonly use a lens system to transmit the image from the distal tip of the endoscope to a viewer. The lens system is typically a relay lens system in the case of rigid endoscopes or a bundle of fiber optics or an objective lens system in the case of flexible endoscopes. In the case of both rigid and flexible conventional endoscopes, the lens or fiber optic system is relatively expensive and is intended to be re-used many times. Therefore, stringent decontamination and disinfection procedures need to be carried out after each use. Furthermore, known fiber endoscopes and rigid endoscopes have limited lens FOV of no more than 100 degrees, and typical conventional flexible digital endoscope FOV is no more than 120 degrees.

Disposable endoscopy is an emerging category of endoscopic instruments that lessen the risk of cross-contamination and hospital acquired diseases. Partially disposable endoscopy systems for hysteroscopy are discussed in U.S. Pat. No. 8,460,182, incorporated by reference herein. A hysteroscope having a disposable probe was offered by Endosee Corporation of Los Altos, Calif., and is now offered by CooperSurgical, Inc. of Trumbull, Conn., a company that acquired EndoSee Corporation. The endoscope has a miniature video camera at the tip of the disposable portion. The tip has a small diameter, which makes it difficult to incorporate a lens system. In the known disposable endoscope, the camera FOV is no more than about 120°, so the user may need to frequently reposition the tip to include different areas of the uterus in the camera FOV. For endoscopes that are suitable for larger or differently shaped organs, such as the bladder, viewing different areas of the bladder interior may require even more frequent repositioning of the camera tip with such an FOV. This is undesirable because it makes the examination longer, and also because it prevents the concurrent viewing of a larger area in the organ.

The endoscope tip includes light sources such as LEDs to illuminate at least a portion of the camera FOV. The illuminated field typically is not the same as the camera FOV, so that some of the camera FOV is not illuminated and thus is not imaged well and/or some of the illumination is wasted in that it does not contribute to imaging because it illuminates an area not currently seen by the camera. In addition, the illumination may impair imaging depending on the position and orientation of the camera relative to the organ being imaged. For example, if one set of LEDs is much closer to the organ wall than another set, one area of the wall can be illuminated more and can appear brighter and even saturate that area of the image, making image assessment more difficult.

The subject matter described or claimed in this patent specification is not limited to embodiments that solve any specific disadvantages or that operate only in environments such as those described above. Rather, the above background is only provided to illustrate one exemplary technology area where some embodiments described herein may be practiced.

SUMMARY

According to some embodiments that are particularly suitable for fields such as urology and endoscopic surgery, a low-cost surgical instrument for examining and injecting a desired fluid into a patient's tissue comprises a single-use, disposable portion that releasably attaches to a multiple-use portion that has a handle configured to be grasped by a user's hand and carries a mechanically attached video screen to thereby form an assembled endoscope. The single-use portion includes a camera or imaging module at a distal part of the single-use portion, where the camera module comprises: a digital image sensor array that is no more than 2.2 mm wide and is configured to send digital video toward the multiple-use portion for display at the video screen; a lens barrel housing a lens stack of no more than, each made of a polymer material, through which the sensor array receives an image, which lens stack presents the sensor array with a diagonal field of view (FOV) of 140 degrees or more when the sensor array is rectangular or square; and two or more LED light sources arranged around the lens barrel and having a field of illumination (FOI) that matches the FOV of the camera module. The single-use portion has an outside dimension no greater than 4.2 mm in cross-section at said distal part thereof, and comprises at least one internal lumen that is configured to pass a guide wire with an outside diameter of 0.8 mm or to pass fluid.

According to some embodiments, the single-use portion further includes one or more of the following features: the lens stack has a front that is no more than 4 mm from a sensor plane of said sensor array; the lens barrel has a diameter of no more than 2 mm; the lens stack causes a spatial distortion of no more than 15% at a peripheral area of said FOV; each of said lenses is made of a polymer material; each of the no more than two lenses is molded; the lens stack has a total track length no greater than 4 mm and is no wider than 2 mm in cross-section; the lens barrel houses an iris; the lens barrel houses an infrared (IR) filter; the LED light sources are arranged symmetrically relative to the lens stack to thereby facilitate coverage of said FOV by said FOI and avoid blind spots; the LED light sources have illumination fields that only partly overlap; the LED sources are mounted on a C-clip that snaps over a distal portion of the lens barrel; the lens barrel includes a light-block ferrule that extends distally from the lens stack and the LED light sources and keeps direct light from said light sources from entering the lens stack; the distal part thereof terminates in a flat central surface and a beveled periphery, and wherein said flat central surface has openings for light from the LED light sources to exit in the distal direction and reflected light to enter said lens barrel, and said beveled peripheral surface has an opening for at least one of said internal lumens.

According to some embodiments, the single-use portion is combined with the multiple-use portion to form an assembled endoscope in which the single-use portion and the multiple-use portion are releasable attached to each other through mechanical and electrical connectors, and the camera module supplies the video screen with images for display thereon.

According to some embodiments, a single-use, disposable portion of an endoscope that releasably attaches to a multiple-use, reusable portion carrying a mechanically attached video screen to thereby form an assembled endoscope, where the single use portion comprises a camera module at a distal part of the single-use portion. The camera module comprises: a digital image sensor array configured to send digital video toward the multiple-use portion for display at the video screen; a lens barrel housing a lens stack through which the sensor array receives an image of a field of view (FOV); two or more LED light sources arranged around the lens barrel and configured to provide a field of illumination (FOI) that matches the FOV of the sensor array. The LED light sources are arranged in two or more sets. A control circuit varies the level of illumination provided by one of the sets relative to the level of illumination provided by another one of the sets to make the light reaching the sensor array more uniform.

In some embodiments, the single-use portion described in the immediately preceding paragraph further includes one or more of the following features: the lens system has only no more than two lenses; and a control circuit varies the level of illumination of one or more of the LED light sources relative to another one or more of the LED sources to make the light reaching the sensor array more uniform.

According to some embodiments, the single-use portion described in either of the two immediately preceding paragraphs is releasably affixed to the multiple-use portion through mechanical and electrical connectors to form an integrated endoscope, which endoscope includes one or more of the following additional features: control circuitry that selectively changes the level of illumination provided by one set of the LED light sources relative to another set thereof; the control circuitry comprises a three-position finger-operated switch having a first position in which the switch causes the first set to provide more illumination than the second set, a second position in which the switch causes the two sets to provide equal illumination, and a third position in which the switch causes the second set to provide more illumination than the first set; the control circuitry comprises a finger-operated rotary switch configured to vary the illumination provided by said two sets from a setting in which the first set provides more illumination and through a range ending with the second set providing more illumination; and the control circuitry comprises a circuit extracting from said digital video a balance signal indicative of the light intensity received at one area of the sensor array relative to another area thereof and a feedback circuit responsive to said balance signal to control the relative level of illumination provided by said LEDs to cause said balance signal to move toward an indication that the two areas of the sensor array receive the same light intensity.

In some embodiment, an endoscope with a single-use, disposable distal portion and a multiple-use, reusable proximal portion, comprises: a handle configured to be grasped by the user's hand and having at least one button controlling endoscope function, a video display screen mechanically carried on the handle, a mechanical connector, and an electrical connector facing in a direction different from that of the mechanical connector, said handle forming a part of said multiple-use portion of the endoscope; a cannula forming a part of the single-use portion of the endoscope and configured with internal lumena; a mechanical connector at a proximal part of the single-use portion of the endoscope, configured to releasably mate tool-free with the mechanical connector at said handle to thereby releasably integrate the single-use portion and the multiple-use portion; an electrical connector extending proximally from said mechanical connector of the disposable portion and configured to mate with the electrical connector at the handle; an imaging module at a distal portion of the cannula, said imaging module comprising a light source illuminating a field of illumination (FOI) and a lens system and a video camera having a field of view (FOV) of more than 120 degrees matching the FOI; wherein the video camera is a digital camera providing a digital signal representing one or more images, and transmits the digital signal from the cannula tip to the video screen at the handle through the mated electrical connectors of the handle and the single-use portion.

In some embodiments, the endoscope described in the immediately preceding paragraph additionally includes one or more of the following features; a field of view (FOV) of more than 130 degrees of the lens system and camera; a field of view (FOV) 140 degrees or more of the lens system and camera; plural LEDs arranged symmetrically relative to a central axis of said distal portion of the camera; and a control circuit selectively varying the relative illumination provided by different ones of the LEDs to improve a brightness balance between different areas of an image displayed at the display.

As used herein, the grammatical conjunctions "and", "or" and "and/or" are all intended to indicate that one or more of the cases, object or subjects they connect may occur or be present. In this way, as used herein the term "or" in all cases indicates an "inclusive or" meaning rather than an "exclusive or" meaning.

As used herein the terms "surgical" or "surgery" refer to any physical intervention on a patient's tissues, and does not necessarily involve cutting a patient's tissues or closure of a previously sustained wound.

BRIEF DESCRIPTION OF THE DRAWINGS

To further clarify the above and other advantages and features of the subject matter of this patent specification, specific examples of embodiments thereof are illustrated in the appended drawings. It should be appreciated that these drawings depict only illustrative embodiments and are therefore not to be considered limiting of the scope of this patent specification or the appended claims. The subject matter hereof will be described and explained with additional specificity and detail through the use of the accompanying drawings in which:

FIGS. 1 and 2 are a right-side view and a top view, respectively, of a handheld surgical endoscope, according to some embodiments;

FIGS. 3A and 3B are perspective views.

FIG. 6B illustrates a mismatch between FOI and FOV in known prior art endoscope.

DETAILED DESCRIPTION

Figure 3C:
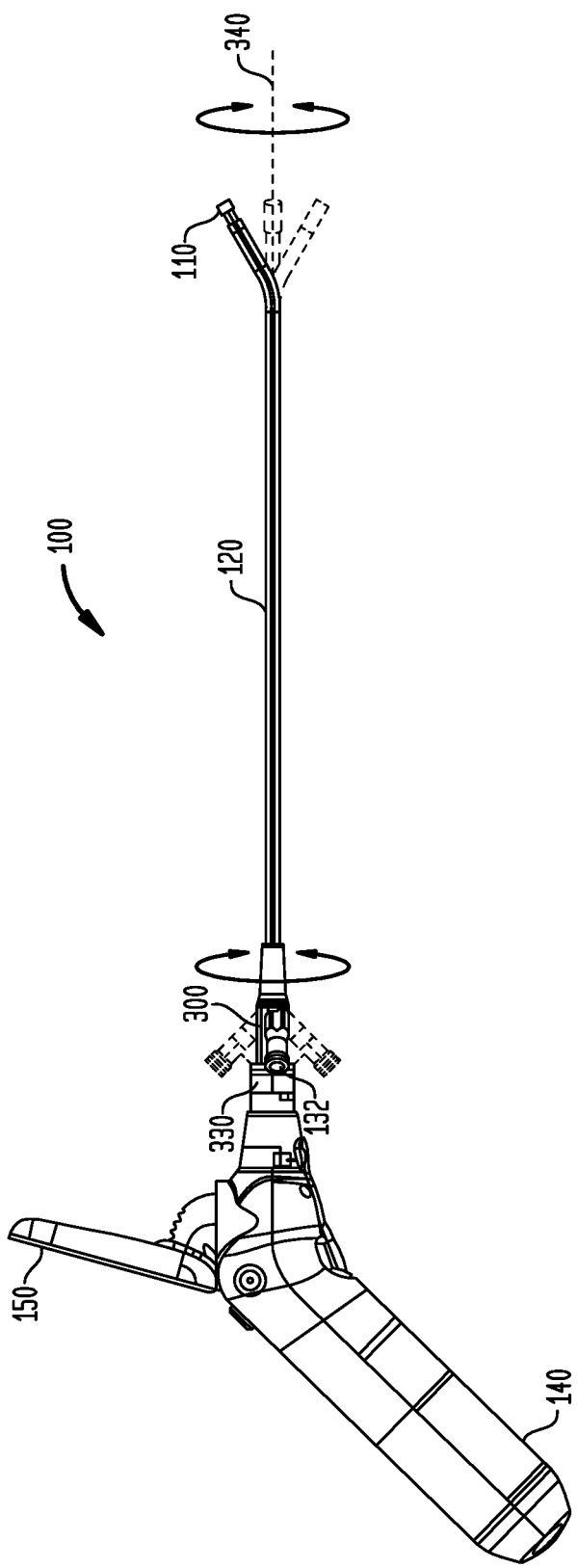
FIG. 3C is a side view.

A detailed description of examples of preferred embodiments is provided below. While several embodiments are described, the new subject matter described in this patent specification is not limited to any one embodiment or combination of embodiments described herein, but instead encompasses numerous alternatives, modifications, and equivalents. In addition, while numerous specific details are set forth in the following description to provide a thorough understanding, some embodiments can be practiced without some or all these details. Moreover, for greater clarity certain technical material that is known in the related art has not been described in detail in order to avoid unnecessarily obscuring the new subject matter described herein. It should be clear that individual features of one or several of the specific embodiments described herein can be used in combination with features of other described embodiments or with other features. Further, like reference numbers and designations in the various drawings indicate like elements.

FIGS. 1 and 2 are a right-side view and a top view, respectively, of a handheld endoscope 100, according to some embodiments. Endoscope 100 includes an elongated cannula 120 with a distal tip 112 for inserting into a hollow organ or cavity of the body. According to some embodiments, a separate tip sub-assembly 110 is attached to the cannula 120 which can be made from an extruded material. Sub-assembly 110 includes an imaging module and one or more LED light sources for viewing the organ or cavity into which it is inserted. Tip 15 of assembly 110 also includes one or more fluid ports. The distal end of cannula 120 can also be slightly bent as shown in bent region 122.

According to some embodiments, cannula 120 includes a fluid channel that is fluidly connected to distal fluid port 132 at fluid hub and connection assembly 130. Port 132 includes a Luer fitting to facilitate leak-free connection of port 132 with various medical fluid components. The fluid channel or lumen in cannula 120 is also connected to a distal facing fluid port of tip assembly 110. According to some embodiments, wires running from the LED light sources and camera module in tip assembly 110 pass through a separate channel in cannula 120. Although no dedicated working channel is provided in this example, an endoscopic guide wire can be passed through the fluid channel in some applications.

Endoscope 100 includes a multiply-use, reusable portion comprising a handle portion 140 that is sized and shaped in a pistol-like fashion for easy grasping by the endoscope operator (e.g. a doctor or other medical professional). A display module 150 is rotatably mounted on handle 140 via bearing 154 which can be a plain bearing made of plastic, and a rubber coated hinge 152. As can be seen in the dotted outlines in FIGS. 1 and 2, the display module 150 can tilt relative to the handle 140 and can rotate about axis 156 relative to handle. 140. Also visible on handle 140 are image capture button 160 and power button 162. According to some embodiments handle 140 and display module 150 are configured to be re-usable and make up reusable, multiple-use portion 102. The fluid hub and connection assembly 130, cannula 120 and tip assembly 110 make up single-use, disposable portion 104 and are made at a relatively low-cost and are intended to be disposed of after a single-use. By making the tip, cannula, fluid hub all single-use, stringent decontamination and disinfection procedures as well as the risk of cross-contamination and hospital acquired diseases can be significantly lessened or avoided. According to some embodiments the disposable, single-use portion (portion 104 shown as a separate item in FIG. 3A) is sterilized, for example, during production and is provided to the user in a sealed sterilized pouch, for ease of storage and handling. Shown in FIGS. 1 and 2 are various dimensions that have been found to be practical for use in some applications, although other dimensions may be used for various applications, and the endoscope is not limited to the illustrated dimensions. The camera module in the tip assembly can have a wide angle of view, such as 140 degrees or more in this example.

FIG. 3A is a perspective view and FIG. 3B is a side view showing aspects of attachment and detachment of single-use and multiple-use portions of a handheld endoscope, according to some embodiments. The single-use portion 104 and multiple-use, reusable portion 102 attach mechanically primarily via mating mechanical connectors 320 and 322. Electrical connection is made via separate mating electrical connectors 310 and 312. The two portions 102 and 104 are attached via translation vertically towards each other. Note that in this example, on assembly 130 the electrical connector 310 and mechanical connector 320 are both separated from the fluid hub 300 that provides fluid communication between fluid port 132 and the fluid channel/lumen of cannula 120. This separation allows for easy and adequate fluid sealing to prevent fluid from fluid hub 300 from penetrating internally towards connectors 310 and 320 and, in addition, provides some protection against any exterior fluid, for example from fluid port 132 from reaching and possibly compromising electrical connectors 310 and 312. Also, the separation between mechanical connector 320 and fluid hub 300 allows for a sleeve bearing 330 to allow for rotating of cannula 120 relative to the proximal portion of assembly 130. The physical separation of the fluid hub 300 and the mechanical and electrical connectors 320 and 310 also provide additional assurance against accidental contamination from fluid hub 300 to the re-usable portion 102. The difference between d1 and d2, or the separation between the electrical and mechanical connectors 310 and 320 allows for the insulated electrical cable to pass intact though the "housing" formed by fluid hub 300, the sleeve bearing 330 and the mechanical connector 320. Since the electrical connector 310 is positioned outside the fluid-containing "housing," the electrical connections between the cable and the connector can be made outside the housing as well. According to some embodiments, the distances d1 and d2 are about 70 mm and 35 mm respectively. According to some embodiments, both distances d1 and d2 are at least 20 mm and according to some other embodiments both distances d1 and d2 are at least 15 mm. Other distances can be used so long as they provide adequate protection from cross-contamination as determined by the overall design of the endoscope and its intended use.

Figure 3D:
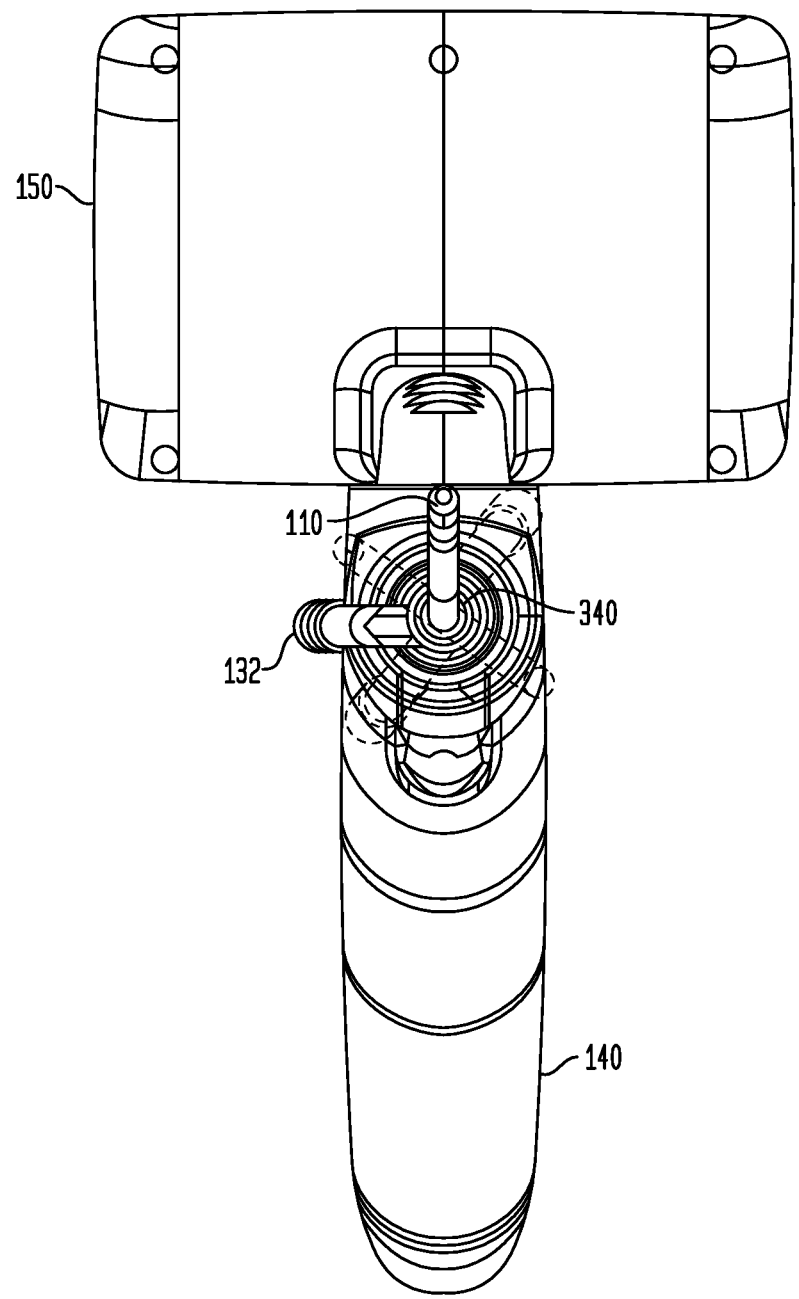
FIG. 3D is a front view, showing aspects of attachment and detachment of single-use and multiple-use portions of a handheld surgical endoscope and of rotation of a single-use portion relative to a multiple-use portion of an endoscope, according to some embodiments.

FIGS. 3C and 3D are side and front views illustrating further aspects of a rotatable cannula used on a handheld endoscope, according to some embodiments. Cannula 120 along with the distal tip 110 and fluid hub 300 are rotatable about the main axis 340. The portion of assembly 130 that rotates with cannula 120 includes the fluid port 132, fluid hub 300 and inner tube that forms the inner portion of sleeve bearing 330. Rotation of cannula 120 can be limited so that the internal electrical cable does not undergo undue stress from twisting. In one example starting from a "neutral" position shown in FIGS. 1 and 2, and in solid lines in FIGS. 3C and 3D, the cannula 120 can be rotated about 180 degrees in either direction (i.e. clockwise and counter clockwise). According to some other embodiments, an asymmetrical rotation pattern can be implemented in sleeve bearing 330 such as 270 degrees in one direction and 90 degrees in another direction. Many other combinations can be implemented, to improve ergonomics for various situations (i.e. various users, types of procedures, and patient anatomy variations). According to some embodiments, the rotation is limited so as not to put undue stress on the internal electrical cable.

Figure 4:
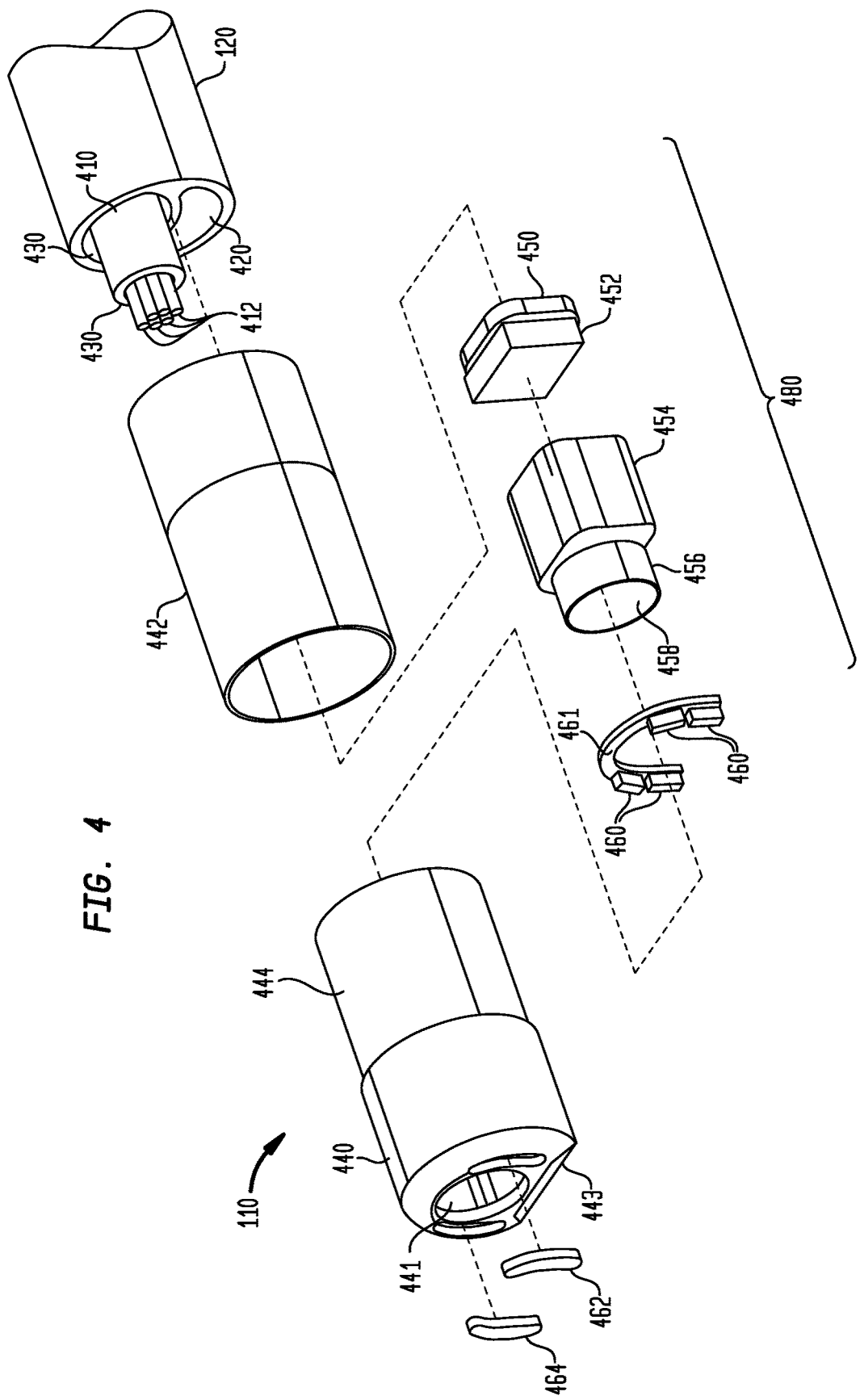
FIG. 4 is an exploded view of a distal part of a single-use portion of an endoscope.

FIG. 4 is an exploded diagram showing various components of a distal tip used on a handheld endoscope, according to some embodiments. Cannula 120 is shown with its upper lumen 430 used to carry cable 410 and lower lumen 420 used to convey fluid. Cable 410 emerges from upper lumen 430 and comprises outer insulation layer 430 surrounding a plurality of inner conductors 412. Each of the inner conductors 412 have their own insulation. Although 6 conductors 412 are depicted in this example, other numbers of conductors can be used depending on the needs to of cameral module and LEDs. The cannula 120 and tip housing 440 are held together using a sleeve 442 that is dimensioned to fit around both the outer surface of the distal end of cannula 120 and the proximal end 444 of tip housing 440. According to some embodiments, sleeve 442 is made of stainless steel, although other material can be used. The three pieces, cannula 120, sleeve 442 and tip housing 440 can be glued together using, for example, a U-V cured bonding glue. Some or all of the conductors 412 are bonded to a printed circuit board (PCB) 450. According to some embodiments, a relatively strong bonding technique, such as solder, is used to attach the conductors 412 to PCB 450. Such strong bonding has a benefit of further reducing risk that the portions of the tip assembly 110 become separated from the cannula during a procedure. Sensor 452 is mounted on PCB 450. A holder 454 sits around sensor 452 and a light shield or ferrule 456 further surrounds the lens system and dust cover 458.

According to some embodiments, plural LEDs 460 are mounted to a horseshoe-shaped (C-clip shaped) LED board 461 that surrounds the distal end of the lens system 458. According to some embodiments, light-guide lenses 462 and 464 are inserted and bonded to recesses in the distal end of tip housing 440. Although 4 LEDs 460 are shown in FIG. 4, other numbers of LEDs can be used around the periphery of lens system 458 such as 1, 2, 3, 4, 5, 6 or more LEDs. By using 4 LEDs, it has been found that a relatively uniform beam pattern can be produced.

By positioning the LEDs inside the housing 440 instead of flush with the distal surface, the LEDs are in a sense "encapsulated" in that they do not contact the patient tissue and are well sealed from fluid such as saline. It has also been found that the translucent shell provides some useful light dispersion for a widespread illumination either with or without the use of lenses 462 and 464. Also, recessing the LEDs as shown frees up some space on the distal surface. Finally, the assembly process is simplified when locating the LEDs inside the housing 440.

The components 480 within an upper cavity of tip housing 440 form a camera or imaging module 480. The tip housing 440 can be molded from a transparent material such as polycarbonate but other easy to mold materials could be used instead. When assembled, the front of lens system 458 sits flush with the distal end of tip housing 440 through lens orifice 441. A lower orifice 443 is provided to allow for fluid communication with lower lumen 420 of cannula 120. Note that port 132, lumen 420 and orifice 443 can be provide fluid in-flow (i.e. flowing fluid out of the endoscope and into the patient's organ or cavity and/or fluid out-flow (i.e. flowing fluid out of the patient's organ or cavity and into the endoscope).

Figure 4A:
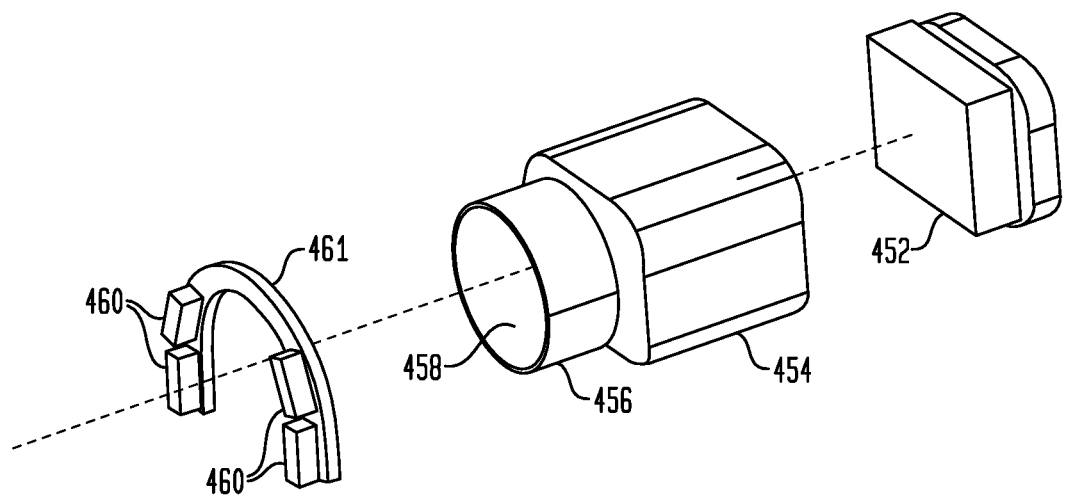
FIG. 4A is a detail of FIG. 4.

FIG. 4A is a magnified perspective view of a portion of the components of camera module 480 illustrated in FIG. 4. LED board 461 is horseshoe-shaped, or shaped as a C-clip, and mounts by snapping over the proximal end of light shield 456, or can be a ring-shaped mount slipped over light-block ring 456. Light shield 456 extends distally from the LEDs and thus serves as a light shield or ferrule that keeps direct light from the LED from reaching the lens system inside holder 454 and sensor 452. Preferably, LEDs 460 are coplanar or nearly coplanar with the distal end of the lens assembly, and comprise a pair of LEDs 460a at one (left) side of light-block ring or sleeve 466 and a pair of LEDs 460b at the other (right) side.

Figure 4B:
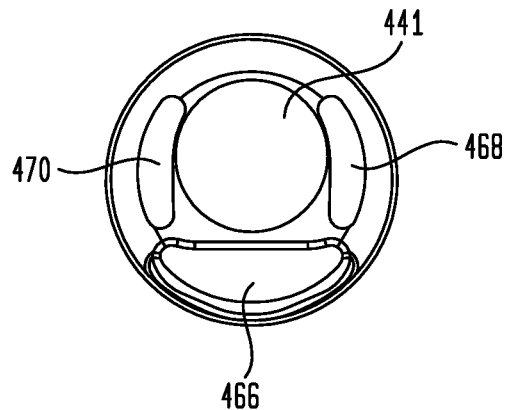
FIGS. 4B, 4C, and 4D are, respectively, a front view, a side view, and a partial sectional view, of the distal tip of a single-use portion of an endoscope, according to some embodiments.
Figure 4C:
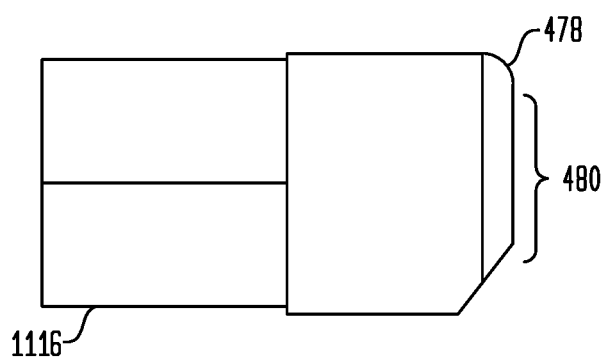
Figure 4D:
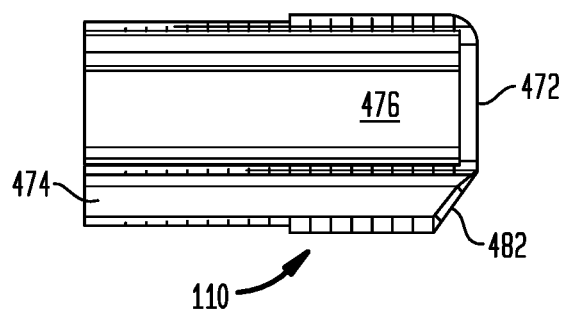

FIG. 4B is a front view, FIG. 4C is a side view, and FIG. 4D is a sectional view of one example of the distal tip of cannula 120. Some dimensions are illustrated but alternative dimensions are possible and contemplated within the scope of this patent specification. FIG. 4B shows lens orifice 441, recesses 468 and 470 into which the lenses 462 and 464 are inserted, and a lower orifice 474 through which fluid can pass into or out of the patient or a guide wire can pass. As can be seen from FIG. 4D, the inner part of the tip 110 of cannula 120 has two cavities 472 and 474 that are separated by wall 476. FIGS. 4C and 4D show that according to some embodiments the distal outer edge 478 is rounded to facilitate insertion in/though tissue passages and alleviate tissue contact issues. When inserting the endoscope into and through passages such as the urethra, trachea or blood vessels, it is desirable that the outer distal edge 478 of the distal tip should be rounded since that region of the distal tip both contacts and dilates the tissue passage. In such cases, the central portion 481 of the distal tip can be made less rounded or flat. Making the central portion 481 less rounded or flat has been found to enhance imaging characteristics over a more spherical overall tip since the camera and illumination are not or significantly less impaired. In the case shown, orifice 472 can be covered with a flat glass dust cover that sits flush with the remainder of central portion 481. FIGS. 4C and 4D show that outer surface of housing 482 around fluid or guide wire opening 466 can be tapered. In the example shown an approximately 1-degree taper has been found to be useful for insertion in urological applications. The tip surface around the fluid or guide wire orifice is beveled, as best seen in FIGS. 4C and 4D.

Figure 5:
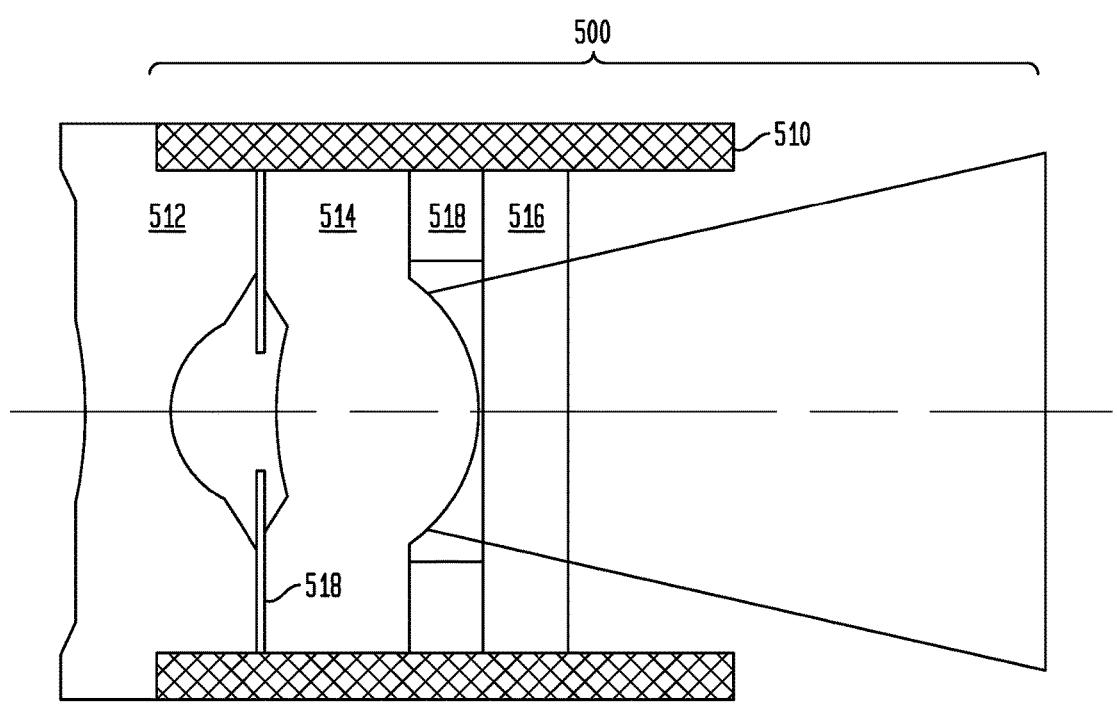
FIG. 5 is a sectional view showing a lens barrel housing a lens system that provides a wide field of view at a sensor plane of an imaging sensor in a single-use portion of an endoscope, according to some embodiments.

FIG. 5 illustrates a section through a lens system 500 comprising a lens barrel 510 that fits in lens holder 454 seen in FIG. 4C and preferably is coaxial with light shield or ferrule 456. Lens barrel 510 holds two lenses 512 and 514, labeled as $1^{st}$ (top) element 512 and $2^{nd}$ element 514. The $2^{nd}$ lens element 514 can be held in barrel 510 by a mounting ring or spacer 516. The $1^{st}$ lens element 512 can be held in barrel 510 by a ring-shaped iris 518. An infrared (IR) filter 516 can be placed just proximally of the $2^{nd}$ element 514. A single lens could be used in place of lenses 512 and 514 if it can provide a sufficiently wide FOV to the camera module.

An important property of the lens system 500 is that it provides sensor 452 with a field of view (FOV) that is uniquely wide for a single-use, disposable endoscope portion with a small outside diameter such as less than 5 mm and preferably is 4.2 mm or less. In some embodiments, the FOV is more than 120°, preferably is 130° or more, and most preferably is 140° or more at a diagonal of a rectangular or square sensor 452, at a sensor plane thereof. In a specific example of a lens system 500 according to some embodiments, for a rectangular sensor 452 the FOV parameters are: diagonal FOV—140°±3°; horizontal FOV—106°±3°; and vertical FOV—82°±3°. In this example, the total track length of lens assembly 500, which is the distance from the distal end of $1^{st}$ lens element 512 to the sensor plane or sensor 452, is 4 mm; the distance from the proximal end of IR filter 516 to the sensor plane of sensor 452 is 1.56 mm; and the distance from the proximal end of lens barrel 510 to the sensor plane is 1.2 mm. The outside diameter of lens barrel 510 is 2 mm in this example. The resolution of the combination of lens system 500 and sensor 452 (in an example of sensor with 640×480 pixels), in terms of MTF (modulation transfer function), is (1) on axis—50% at 200 lp/mm (line pairs per mm), and 76% at 100 lp/mm; and (2) for 80%–39% (t) and 52% (s) at 100 lp/mm, and 66% (t) and 74% (s) at 60 lp/mm in the same example. The distortion is no more than 15% in the same example. Of course, these parameters are for a specific example of some embodiments, and different parameters can be used and are contemplated in this patent specification so long as they achieve the desired FOV greater than 120°, preferably 130° or more, and most preferably 140° or more.

The wide field of view of lens system 510 allows a greater area of the organ being imaged to be seen in a single image than in known prior art disposable endoscopes. This can be particularly important when viewing organs such as the bladder, which has an internal area several times that of the uterus. If a known prior art disposable endoscope with an FOV of 120° is used for viewing the bladder, it would require considerably more repositioning than an endoscope with a wider FOV to examine the same internal area. In addition, the wider FOV allows a greater area of the organ to be seen in a single image, which can facilitate accurate assessment by allowing comparison of one area of the organ relative to other areas in the same image.

Figure 6A:
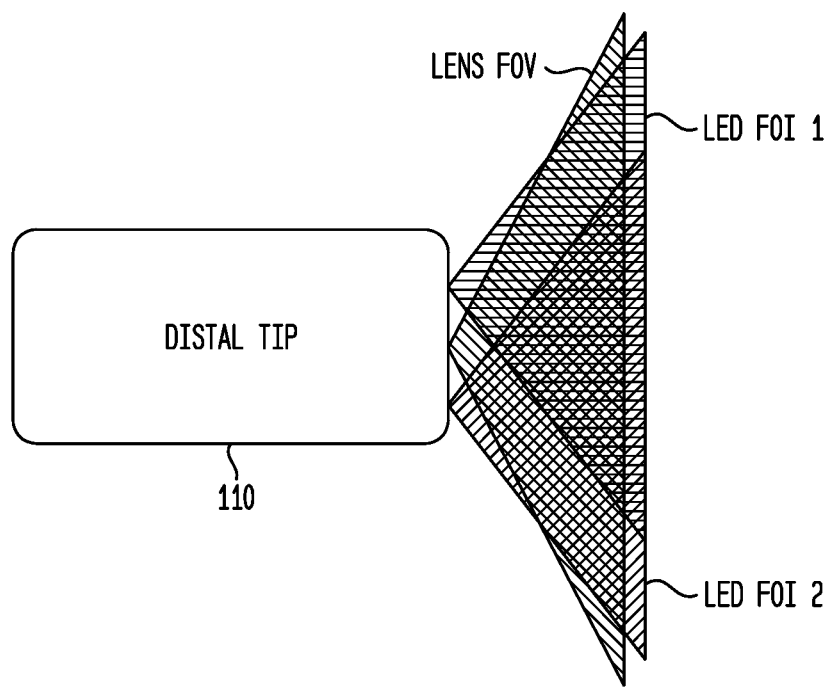
FIG. 6A is a schematic illustration of matching field of illumination (FOI) and field of view (FOV), according to some embodiments.

As illustrated in FIG. 4A and discussed above, according to some embodiments LEDs 460 are symmetrically arranged around light-block ring 456, in a way that allows the illumination from one side of ring 456 to overlap with that from the other side and thus provide a wide field of illumination (FOI) that substantially match the FOV of sensor 452. FIG. 6A illustrates this overlap, where the light from LEDs 460 that are at one lateral side of ring 458 provides a field of illumination labeled LED FOI 1, the light from LEDs 460 that are at the opposite lateral side of ring 458 provides a field of illumination labeled LED FOI 2, and the two FOIs overlap each other and in addition match the FOV of lens system 500. While as illustrated the outer edges of the FOI and the FOV may be slightly offset, they still match to make good use of the available light and avoid blind spots.

In contrast, in a known endoscope the LED light source is not symmetrically arranged relative to the lens system, and there is a substantial mismatch, as illustrated in FIG. 6B, where a substantial portion of the lens FOV is not illuminated and thus there a blind spot with insufficient light to show well in the image. When referring to a symmetric arrangement of LEDs, this patent specification means a substantially rather than perfectly symmetric arrangement, for example as illustrated in FIG. 4A, where the LEDs are symmetric relative to a vertical section through the central axis of light shield 456 and are nearly but not necessarily perfectly symmetric relative to a horizontal section through the central axis.

Figure 6C:
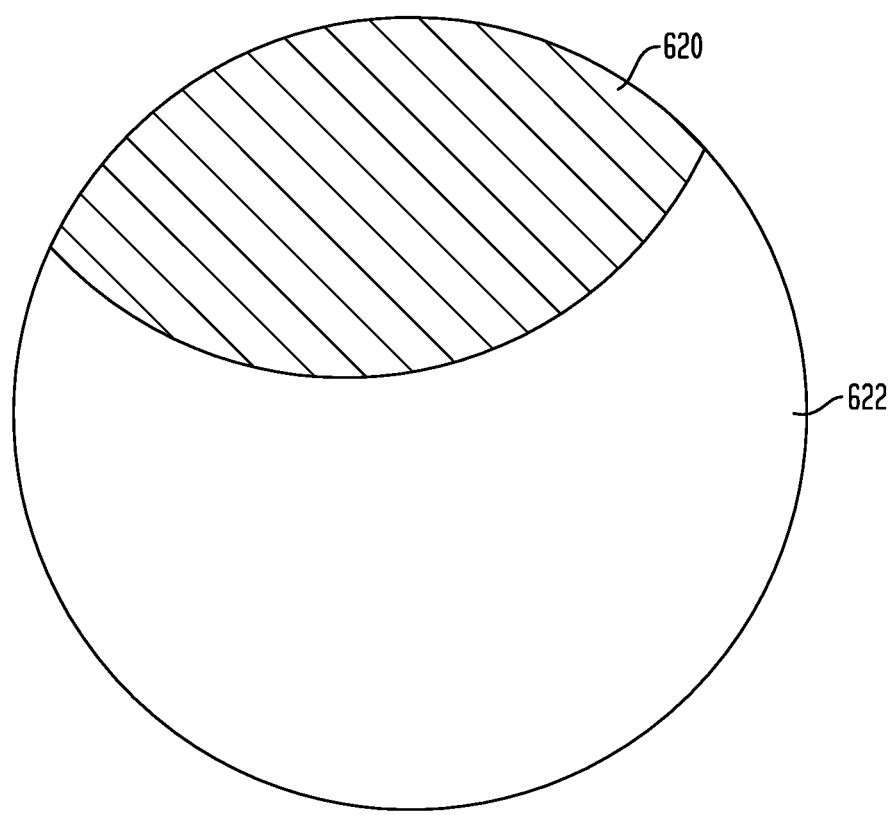
FIG. 6C is a schematic view of an image with imbalance in overall brightness between areas of the image due to mismatch of FOI and FOV and/or due to different distances of LEDs from the surface being imaged.

According to some embodiments, images are improved by providing the endoscope with facilities to make illumination of the camera FOV more uniform. This is particularly beneficial for examining organs such as the internal wall of the bladder, where cannula tip 110 may be in a position in which one pair of adjacent LED is significantly closer to the bladder wall that the other pair. In that situation, one side of sensor 452 may receive significantly more light than the other, and the image may be unbalanced in brightness. This can make image interpretation more difficult as some of the imaged portion of the bladder wall may appear darker than another portion or one portion may appear washed out. FIG. 6C illustrates an image where the field of view of the camera is not uniformly illuminated, and as a result an image region 622 is darker overall because it has received less light than image region 624. This can occur because of a significant mismatch between the FOI and the FOV due to an arrangement such as seen in FIG. 6B. It has been found that uneven overall brightness of areas within an image can occur to a lesser extent for a different reason as well—because some of the LEDs are significantly closer to the organ surface being imaged than other LEDs even when the LEDs are symmetrically arranged around the optical axis of the lens system.

Figure 7:
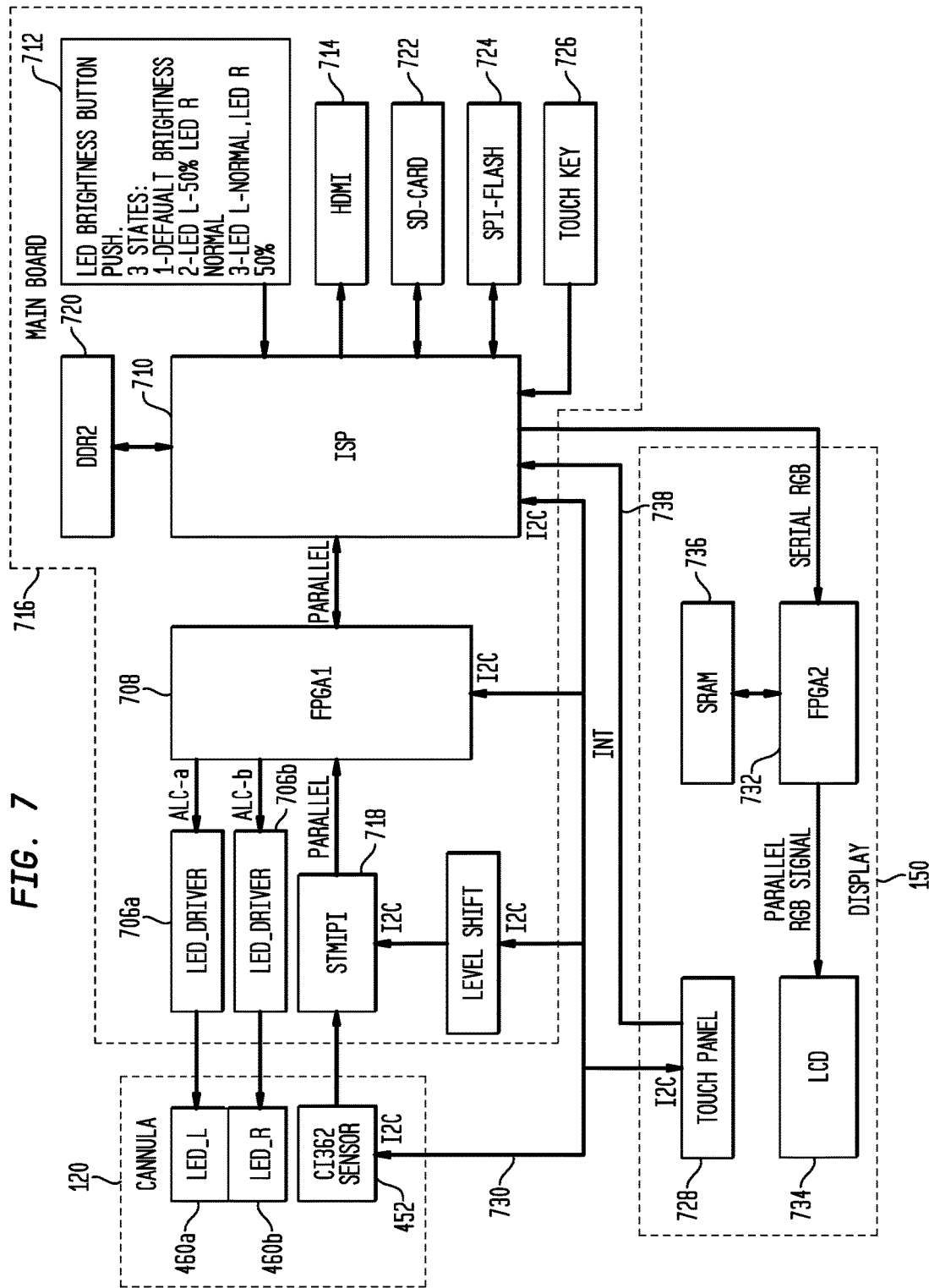
FIG. 7 illustrates an example of a control circuit for equalizing illumination and image brightness balance under manual control, according to some embodiments.

FIG. 7 shows in block diagram form an example of a control circuit or system that can improve brightness balance in the image when different area of the organ being imaged receive different levels of illumination. This control circuit can be used in any of the endoscopes described in this patent specification. FIG. 7 is similar to FIG. 15 in application Ser. No. 15/651,526, incorporated by reference, except for additions and changes that deal with improving brightness balance. Specifically, LEDs 460a at one side of light-shield ring 456 of camera module 480 have their own LED driver 706a and LEDs 460b at the other side of the light-shield ring have their own LED driver 706b. Field programmable gate array 708 provides respective control signals ALCa and ALCb to LED drivers 706a and 706b that vary the intensity of light the LEDs put out. A 3-position, manually operated switch or button 712 provides input to processor ISP 710, which through FPGA 708 varies the control signals ALCa and ALCb and thus the light intensity from LEDs 460a and 460b. As one example, (i) in position 1 of switch 712, which can be the default position, LEDs 460a and 460b provide roughly equal light intensities, e.g., each operates at 100% of its rated brightness; (ii) in position 2, LEDs 460a operate at 50% of their rated brightness while LEDs 460b operate at 100% brightness, and (iii) in position 3, LEDs 460a operate at 100% brightness while LEDs 460b operate at 50% brightness. Of course, different brightness levels can be implemented for the dimmed LEDs, such as 40%, 60%, 70%, etc. And, there can be more than two individually controlled groups of LEDs, such as 3 or 4 groups, with a corresponding switch having more positions that vary the light outputs of the LEDs. A potentiometer rather than a 3-position switch can be used to make the steps in relative light output of the LEDs even finer. Switch or button 712 can be mounted at a convenient position on handle 140, for example as illustrated in FIG. 1, to be operated by the user. While display 150 shows an image and the user is manipulating handle 140 to point cannula 120 to different areas of the organ being examined, the user can operate switch 712 depending on the brightness balance seen on display 150.

In other respects, FIG. 7 is like FIG. 15 in said application Ser. No. 15/651,526, and will be similarly described below except for the use of different reference numerals. A main board 716 serves to interface, process the data, and control the components at the tip of cannula 120 and display module 150. In broad terms, main board 716 supplies power and control signals to camera module 480 and LEDs 460 as well as to display module 150, and converts the camera output to an image signal for display on display module 150. In main board 716, processor 710 (which can be a DSP or ISP) digital signal processor, controls the operation of the components at the tip of cannula 120 and in display module 150 and processes the captured image data. Communicating through field programmable gate array (FPGA1) 708, processor 710 sends control signals ALCa and ALCb to LED-DRIVERs 706a and 706b, respectively, to turn LEDs 460a and 460b ON and OFF and to adjust their outputs to the desired brightness levels as needed. Processor 710 receives the output of camera module 480 after it has been converted from serial to parallel by a STMIPI interface 718. Processor 710 exchanges information as needed with information storage devices such as DDR2 memory 720, SD-CARD memory 722, and SPI-FLASH memory 724. Processor 710 can provide an output to HDMI connector 714 and can receive key actuation or interrupt signals from touch keys 726, which can be buttons on handle 140 such as buttons 160 and 162. Processor 710 also receives touch or swipe information from touch panel 728 in display 150. Processor 710 provides control signals over I2C line 730 to cameral module 480, touch panel 728, and FPGA1 708. Processor 710 converts the parallel signal from FPAG1 708 to a serial RGB signal and supplies the serial RGB signal to display module 150.

Display module 150 displays images from camera module 480 and responds to touch to send control signals to processor 710. Display module 150 comprises a field programmable gate array (FPGA2) 732 that receives images from camera module 480 that are provided through processor 710 in serial RGB format. FPGA2 732 sends the images, in parallel RGB format, to LCD display screen 734, and can store selected images in memory SRAM 736 and recall them for display or for storage in SD-CARD 722 and/or SPI-FLASH 724, in response to commands from touch panel 728 or preprogrammed instructions from processor 710 or FPGA2 732 or other processor or memory components. Touch panel 728 communicates with processor 710 over signal bus I2C 730 and can send commands to processor 710 over a direct bus INT 738. Power supply facilities such as a connection to a rechargeable battery removably secured to handle 140, a connection to a manual OFF/ON switch on handle 140, and to a camera control button on handle 140 also can be on main board 716.

Figure 8:
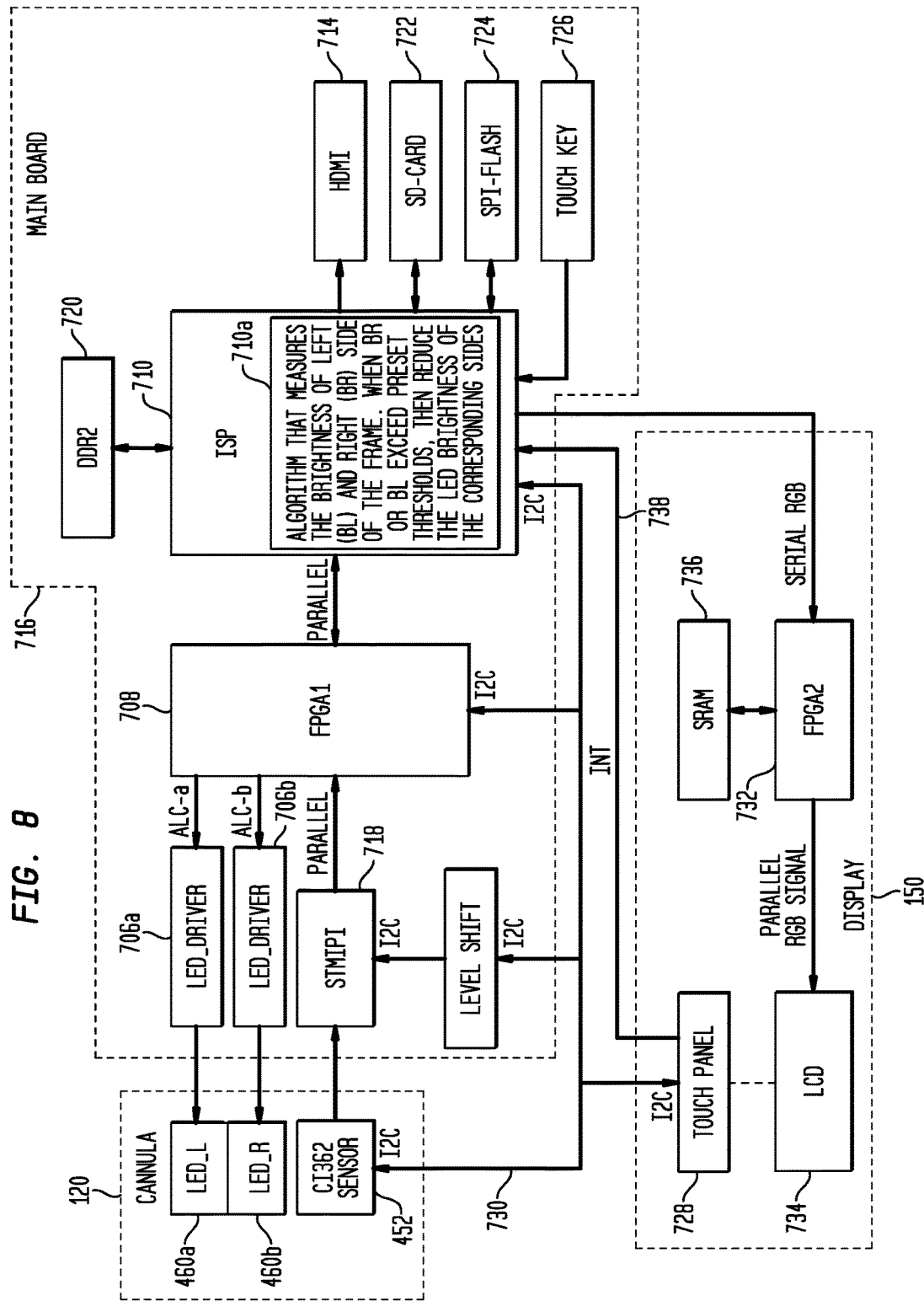
FIG. 8 illustrates an example of a control circuit for automatically equalizing image brightness, according to some embodiments.

According to some embodiments, an automated system can be implemented in any of the described endoscopes to improve brightness balance in the image. FIG. 8 illustrates such an automated system, and is otherwise similar to FIG. 7 except that it omits switch 712 and includes an algorithm in processor 710 that responds to the level of overall brightness in selected areas of the image information from sensor 452 (or from LCD display 734) to change the light outputs of LEDs 460 toward equalizing the overall brightness over the entire image on LCD display 734. In this example, processor 710 is programmed with an algorithm 710a that responds to a difference in the overall brightness of two different areas of the current image frame from sensor 452, for example to a difference between the overall brightness of the left half of the image frame and the right half. The algorithm can be relatively simple—e.g., when either of the left half or the right half of the image frame exceeds a selected threshold of overall brightness, processor 710 calculates a balance signal indicative or the difference and issues commands to LED driver 706a and/or 706b to reduce the intensity of the LEDs that correspond to the side of the image that had has overall brightness over the threshold. In a simple implementation, algorithm 710a can mimic the effect of switch 712 of FIG. 7, i.e., (i) when the left side of the image frame is more than a threshold brighter than the right side, reduce the light output of the left LEDs 460a by 50% (or some other selected % reduction), (ii) do the opposite if the right side of the image has overall brightness over a threshold, and (iii) do not change the relative outputs of the LEDs is the difference in overall brightness of the left and right sides of the image frame is within a selected threshold. Alternatively, algorithm 710a can provide control in finer steps, e.g., if the difference in overall brightness between the two halves of the image frame is more than a first threshold but less than a second threshold, decrease the light output of the relevant LEDs by a first amount; but if the difference is more than a second, greater threshold, decrease by a second, greater amount. There can be even more steps, i.e. three or more thresholds and three or more corresponding decreases in the light output of the relevant LEDs. The algorithm can be implemented by a person of ordinary skill in programming given the teachings of this patent specification. Instead of responding to overall brightness or each half of the image frame, algorithm 710a can be configured to respond to two or more smaller areas of the image, such as two strips of the image frame or two groups of pixels spread in each half of the image.

Although the foregoing has been described in some detail for purposes of clarity, it will be apparent that certain changes and modifications may be made without departing from the principles thereof. It should be noted that there are many alternative ways of implementing both the processes and apparatuses described herein. Accordingly, the present embodiments are to be considered as illustrative and not restrictive, and the body of work described herein is not to be limited to the details given herein, which may be modified within the scope and equivalents of the appended claims.

What it claimed is:

1. An endoscope that comprises:
   a single-use, disposable portion and a multiple-use, reusable portion to which the single-use portion releasably attaches, wherein:
   the reusable portion has a handle configured to be grasped by a user and carries a mechanically attached video screen to thereby form an assembled, one-piece endoscope when the single-use portion is attached thereto, which one-piece endoscope is entirely hand-held when in use in a patient procedure, the handle further including a mechanical connector at a distal portion of the handle and an electrical connector that is spaced in the proximal direction from the mechanical connector and faces in a direction transverse to a distal direction opposite said proximal direction;
   said single-use portion comprises:
      a camera module at a distal part of said single-use portion, said camera module comprising:
         a digital image sensor array that is no more than 2.2 mm wide and is configured to send digital video toward said multiple-use portion for display at said video screen;
         a lens barrel housing a lens stack of at most two single lenses, made of a plastic material, through which the sensor array receives an image, which lens stack presents the camera module with a diagonal field of view (FOV) of 140 degrees or more;
         two or more LED light sources arranged around the lens barrel and having a field of illumination (FOI) that matches in area the FOV of the camera module;
   wherein said single-use portion:
   has an outside dimension no greater than 4.2 mm in cross-section at said distal part thereof;
   comprises at least one internal lumen configured to pass a guide wire with an outside diameter of 0.8 mm or to pass fluid; and
   includes a mechanical connector and electrical connector that are both operable to mate with the mechanical connector and electrical connector of the handle, respectively, by movement in the direction transverse to a distal direction opposite said proximal direction.

2. The endoscope of claim 1, wherein said lens stack has a front that is no more than 4 mm from a sensor plane of said sensor array.

3. The endoscope of claim 1, wherein said lens barrel has a diameter of no more than 2 mm.

4. The endoscope of claim 1, wherein said lens stack causes a spatial distortion of no more than 15% at a peripheral area of said FOV.

5. The endoscope of claim 1, wherein each of said lenses is made of a polymer material.

6. The endoscope of claim 1, wherein each of said lenses is molded.

7. The endoscope of claim 1, wherein said lens stack has a total track length no greater than 4 mm and is no wider than 2 mm in cross-section.

8. The endoscope of claim 1, wherein said lens barrel further houses an iris.

9. The endoscope of claim 1, wherein said lens barrel further houses an infrared (IR) filter.

10. The endoscope of claim 1, wherein said LED light sources are arranged symmetrically relative to the lens stack to match said FOI and FOV to avoid blind spots or unevenly illuminated FOV.

11. The endoscope of claim 1, wherein said LED light sources have illumination fields that only partly overlap.

12. The endoscope of claim 1, further including a C-clip or an O-ring on which said LED light sources are mounted and which fits over a distal portion of said lens barrel.

13. The endoscope of claim 1, further including a light-block sleeve that extends distally from the lens stack and said LED light sources to keep direct light from said light sources from entering the lens stack.

14. The endoscope of claim 1, wherein said distal part thereof terminates in a flat central surface that covers the entire lens barrel, and a beveled or rounded periphery.

15. The endoscope of claim 1, releasably attached to said multiple-use portion with mechanical and electrical connectors on each of said portions, to form an assembled endoscope.

16. An endoscope with a single-use, disposable distal portion and a multiple-use, reusable proximal portion, comprising:
   a handle configured to be grasped by a user's hand and having at least one button controlling endoscope functions, a mechanical connector at a distal portion of the handle, an electrical connector that is spaced in the proximal direction from the mechanical connector and faces in a direction transverse to a distal direction opposite said proximal direction, and a video display screen mechanically attached to and carried by the handle, wherein the handle with said at least one button, connectors, and screen form a part of the multiple-use portion of the endoscope;
   a cannula forming a part of the single-use portion of the endoscope and configured with internal lumina;
   a mechanical connector and an electrical connector at a proximal part of the single-use portion of the endoscope, configured to releasably mate tool-free with the mechanical connector and the electrical connector, respectively, at the multiple-use portion of the endoscope to thereby releasably integrate the multiple-use and the single-use portions to form an endoscope that is entirely hand-held, wherein the mechanical connector and electrical connector of the single-use portion are both operable to mate with the mechanical connector and electrical connector of the handle, respectively, by movement in the direction transverse to a distal direction opposite said proximal direction;
   a light source and an imaging module with a video camera at a distal portion of the cannula, coupled with the screen through said electrical connectors to illuminate a region in the patient and provide images of the region to the screen under the control of said at least one button at the handle;
   said imaging module comprising a lens system configured to provide imaging module with a field of view (FOV) of more than 120 degrees; wherein the video camera is a digital camera providing a digital signal representing one or more images, and transmits the digital signal from the cannula tip to the handle.

17. The endoscope of claim 16, in which said lens system is configured to provide the imaging module with a field of view (FOV) of more than 130 degrees.

18. The endoscope of claim 16, in which said lens system configured to provide the imaging module with a field of view (FOV) of 140 degrees or more.

19. The endoscope of claim 16, in which said light source comprises plural LEDs arranged symmetrically relative to an optical axis of said lens system.

20. The endoscope of claim 16, in which said light source comprises plural LEDs and further including a control circuit selectively varying the relative illumination provided by different ones of the LEDs to improve a brightness balance between different areas of an image displayed at said display.

* * * * *